(12) United States Patent
Mohammadi

(10) Patent No.: US 6,548,074 B1
(45) Date of Patent: Apr. 15, 2003

(54) SILICONE ELASTOMER EMULSIONS STABILIZED WITH PENTYLENE GLYCOL

(75) Inventor: Fatemeh Mohammadi, Hebron, CT (US)

(73) Assignee: Elizabeth Arden Co., division of Conopco, Inc., New York, NY (US)

( * ) Notice: Subject to any disclaimer, the term of this patent is extended or adjusted under 35 U.S.C. 154(b) by 0 days.

(21) Appl. No.: 09/533,876

(22) Filed: Mar. 22, 2000

Related U.S. Application Data

(60) Provisional application No. 60/145,128, filed on Jul. 22, 1999.

(51) Int. Cl.$^7$ .......................... A61K 7/00; A61K 31/695
(52) U.S. Cl. .......................... 424/401; 514/63
(58) Field of Search .............................. 424/401; 514/63

(56) References Cited

U.S. PATENT DOCUMENTS 5,833,973 A    11/1998   Dobkowski et al.

FOREIGN PATENT DOCUMENTS

| EP | 404532   | * | 12/1990 |
| EP | 0 917 870 |   | 11/1997 |
| EP | 0 850 640 |   | 12/1997 |
| EP | 0 925 783 |   | 12/1998 |
| EP | 0 935 960 |   | 1/1999  |
| EP | 917870   | * | 5/1999  |
| WO | 95/01151 |   | 1/1995  |
| WO | 96/11572 |   | 4/1996  |
| WO | 97/30692 |   | 8/1997  |
| WO | 97/32561 |   | 9/1997  |
| WO | 98/00105 |   | 1/1998  |

OTHER PUBLICATIONS

Dragoco Brochure—Sep. 1998.

* cited by examiner

*Primary Examiner*—Alton Pryor
(74) *Attorney, Agent, or Firm*—Herbert Dubno

(57) ABSTRACT

Cosmetic compositions are provided which include a silicone elastomer, a volatile siloxane, water and pentylene glycol. These compositions are emulsions which have improved phase stability as a result of the presence of pentylene glycol. The systems are also microbiologically preserved without the need for other added traditional preservatives.

7 Claims, No Drawings

SILICONE ELASTOMER EMULSIONS STABILIZED WITH PENTYLENE GLYCOL

This application claims the benefit of Provisional Application No. 60/145,128 filed Jul. 22, 1999.

BACKGROUND OF THE INVENTION

1. Field of the Invention

The invention relates to silicone elastomer cosmetic emulsions stabilized against separation.

2. The Related Art

Cosmetic emulsions of silicone elastomers have become quite popular in cosmetic formulations.

U.S. Pat. No. 5,387,417 (Rentsch) reports obtaining cosmetically acceptable, translucent moisturizing lotions through emulsification of a petrolatum base with a crosslinked organopolysiloxane-polyoxyalkylene emulsifier. According to the disclosure, not only is compatibility achieved but this siloxane allows for matching of refractive indices for the continuous and discontinuous phases.

U.S. Pat. No. 5,280,019 (Klimisch) reports compositions which enhance the absorption and retention of moisturizer on the skin. These results are achieved through use of an organosilicon compound which is a carboxy functionalized polysiloxane or its metal carboxylate salt.

U.S. Pat. No. 5,833,973 (Dobkowski) describes crosslinked elastomeric silicones in aqueous emulsion cosmetic compositions. Inclusion of the elastomer provides a unique liquid/powdery feel when rubbed into the skin.

WO 97/32561 (Nawaz et al.) reports a skincare composition which includes a silicone-containing phase with a crosslinked polyorganosiloxane polymer and silicone oil, an organic liquid crystal-forming amphiphilic surfactant and water.

Emulsions generally have phase stability problems. Some silicone elastomers can improve phase stability. Nevertheless there still remains significant area for improvement.

Accordingly, it is an object of the present invention to provide a cosmetic composition in emulsion form which exhibits good phase stability.

Another object of the present invention is to provide a cosmetic composition in emulsion form which provides improved skinfeel properties.

Still another object of the present invention is to provide a cosmetic composition in emulsion form which is self preserving without requiring the addition of standard preservatives.

These and other objects of the present invention will become more readily apparent from the following summary and detailed description.

SUMMARY OF THE INVENTION

A cosmetic composition is provided which includes:

(i) from about 0.1 to about 30% of a polysiloxane elastomer;

(ii) from about 5 to about 80% of a volatile siloxane;

(iii) from about 10 to about 95% by weight of water; and (iv) from about 0.1 to about 40% by weight of pentylene glycol.

DETAILED DESCRIPTION OF THE INVENTION

Now it has been found that pentylene glycol can stabilize an emulsion combination of silicone elastomer, volatile cyclomethicone and water.

Polysiloxane elastomers are a first essential element of this invention. Advantageously these elastomers will be of the crosslinked type. Even more preferably the elastomers are non-emulsifying although the invention is considered broader than these particular materials. They will have an average number molecular weight in excess of 2,000, preferably in excess of 1,000,000 and optimally will range from 10,000 to 20 million. The term "non-emulsifying" defines a siloxane from which polyoxyalkylene units are absent. Advantageously the elastomers are formed from a divinyl compound, particularly a polymer with at least two free vinyl groups, reacting with Si—H linkages of a polysiloxane backbone such as a molecularly spherical MQ resin. Elastomer compositions are commercially available from the General Electric Company under product designation General Electric Silicone 1229 with proposed CTFA name of Cyclomethicone and Dimethicohe/Vinyl Dimethicone Cross Polymer, delivered as 20–35% elastomer in a cyclomethitcone carrier. A related elastomer composition under the CTFA name of Crosslinked Stea Methyl Dimethyl Siloxane Coplymer is available from Grant Industries, Inc., Elmwood Park, N.J. A still further commercial source for polysiloxane elastomers is available from the Dow Corning Company under the product designation DC 9090, which blends silicone elastomer powder with cyclomethicone.

Amounts of the elastomer may range from about 0.1 to about 30%, optimally from about 1 to about 15%, most preferably from about 3 to about 10% by weight.

A second essential element of the present invention is that of a volatile siloxane. The term "volatile" refers to those materials having a measurable pressure at ambient conditions. Volatile polyorganosiloxanes useful herein may be cyclic or linear. Preferred cyclic silicones include polydimethylsiloxanes containing from about 3 to about 9 silicon Atoms, preferably containing from about 4 to about 5 silicon atoms, generally known as Cyclomethicones. Preferred linear silicone oils include the polydimethylsiloxanes containing from about 3 to about 9 silicon atoms. The linear volatile silicones generally have viscosities of less than about 5 centistokes at 25° C. while the cyclic materials have viscosities of less than about 10 centistokes, the preferable range being from 0.1 to 8 centistokes. Examples of silicone oils useful in the present invention include: Dow Corning 244, Dow Corning 245, Dow Corning 344, Dow Corning 345 and Dow Corning 200 (manufactured by the Dow Corning Corporation); Silicone 7207 and Silicone 7158 C manufactured by the Union Carbide Corporation); and SF1202 (manufactured by the General Electric Company).

Amounts of the volatile siloxane may range from about 5 to about 80%, preferably from about 15 to about 70%, optimally from about 30 to about 65% by weight.

Cosmetic compositions of the present invention will contain substantial levels of water. Emulsions of the present invention will contain water in amounts ranging from about 10 to about 95%, preferably from about 25 to about 80%, optimally from about 35% to about 65% by weight. The emulsions may be of the oil-in-water, water-in-oil or duplex variety. Most especially, the invention is concerned with the water-in-oil variety. Aqueous to oily phases will range in weight from about 10:1 to about 1:10, preferably from about 1:1 to about 2:1, optimally from about 1:1 to about 1.5:1.

Most preferable for the present invention are water-in-oil emulsions having a high internal (water) phase volume.

A final essential element of the compositions according to this invention is pentylene glycol. This material is chemically known as 1,2-pentanediol and available from Dragoco under the trademark Hydrolite-5. Amounts of pentylene glycol may range from about 0.1 to about 40%, preferably from about 0.8 to about 20%, optimally from 1 to about 8% by weight.

Compositions of the invention may optionally contain a skin conditioning agent. The agents may be selected from humectants, exfoliants or emollients.

Humectants are polyhydric alcohols intended for moisturizing, reducing scaling and stimulating removal of built-up scale from the skin. Typical polyhydric alcohols include polyalkylene glycols and more preferably alkylene polyols and their derivatives. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerin and mixtures thereof. Most preferably the humectant is glycerin. Amounts of humectant may range anywhere from about 1 to about 50%, preferably from about 10 to about 40%, optimally from about 25 to about 35% by weight.

Exfoliants according to the present invention may be selected from alpha-hydroxycarboxylic acids, beta-hydroxycarboxylic acids and salts of these acids. Most preferred are glycolic, lactic and salicylic acids and their ammonium or alkali metal salts.

When the conditioning agent is an emollient it may be selected from hydrocarbons, fatty acids, fatty alcohols and esters. Petrolatum is the most preferred hydrocarbon type of emollient conditioning agent. Other hydrocarbons that may be employed include mineral oil, polyolefins such as polydecene, and paraffins such as isohexadecane (e.g. Permethyl 99® and Permethyl 101®).

Fatty acids and alcohols will have from 10 to 30 carbon atoms. Illustrative of this category are pelargonic, lauric, myristic, palmitic, stearic, isostearic, hydroxystearic, oleic, linoleic, ricinoleic, arachidic, behenic and erucic acids and alcohols.

Oily ester emollients may be those selected from one or more of the following classes:

1. Triglyceride esters such as vegetable and animal fats and oils. Examples include castor oil, cocoa butter, safflower oil, cottonseed oil, corn oil, olive oil, cod liver oil, almond oil, avocado oil, palm oil, sesame oil, squalane, Kikui oil, maleated soybean oil and soybean oil.
2. Acetoglyceride esters, such as acetylated monoglycerides.
3. Ethoxylated glycerides, such as ethoxylated glyceryl monostearate.
4. Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.
5. Alkenyl esters of fatty acids having 10 to 20 carbon atoms. Examples thereof include oleyl myristate, oleyl stearate, and oleyl oleate.
6. Ether-esters such as fatty acid esters of ethoxylated fatty alcohols.
7. Polyhydric alcohol esters. Ethylene glycol mono and di-fatty acid esters, diethylene glycol mono- and di-fatty acid esters, polyethylene glycol (200-6000) mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol polyfatty esters, ethoxylated glyceryl monostearate, 1,20-butylene glycol monostearate, 1,2-butylene glycol distearate, polyoxyethylene polyol fatty acid ester, sorbitan fatty acid esters, and polyoxyethylene sorbitan fatty acid esters are satisfactory polyhydric alcohol esters.
8. Wax esters such as beeswax, spermaceti, myristyl myristate, stearyl stearate.

Amounts of the skin conditioning agent may range from about 1 to about 50%, preferably from about 3 to about 25%, optimally from about 5 to about 20% by weight.

Surfactants may be a further component of compositions according to the present invention. These may be selected from nonionic, anionic, cationic or amphoteric emulsifying agents. They may range in amount anywhere from about 0.1 to about 30%, preferably from about 0.5 to about 15%, optimally from about 1 to about 10% by weight.

Illustrative nonionic surfactants are alkoxylated compounds based on $C_{10}$–$C_{22}$ fatty alcohols and acids and sorbitan. These materials are available, for instance, from the Shell Chemical Company under the Neodol trademark. Copolymers of polyoxypropylene-polyoxyethylene, sold by the BASF Corporation under the Pluronic trademark are sometimes useful. Alkyl polyglycosides available from the Henkel Corporation may also be utilized for purposes of this invention.

Anionic type surfactants include the ammonium, alkali and alkaline earth metal salts of fatty acids (soaps), lauryl sulphates, lauryl ether sulphates, alkyl benzene sulphonates, sarcosinates, taurates, mono- and di-alkyl acid phosphates and fatty acyl isethionates.

Amphoteric surfactants include such materials as dialkylamine oxide and various types of betaines (such as cocamidopropyl betaine and cocoamphoacetates).

Particularly preferred are combinations of a $C_{16}$–$C_{20}$ fatty alcohol or acid (hydrophobe portion) alkoxylated with from about 1 to about 5 moles of ethylene or propylene oxide and a second hydrophobe portion alkoxylated with from about 10 to about 40 moles of ethylene or propylene oxide. These high and low HLB nonionic combinations should be in a ratio from about 10:1 to about 1:10, preferably from about 2:1 to about 1:2, optimally about 1:1. An anionic co-surfactant such as a $C_8$–$C_{20}$ alkyl phosphate salt is also preferably present. The ratio of the total nonionic to anionic surfactants may range from about 20:1 to about 1:2, preferably from about 10:1 to about 1:1, optimally from about 5:1 to about 2:1 by weight. An illustrative combination of nonionics and anionic surfactants is steareth-2, steareth-21 and cetearyl phosphate (available as Amphisol A®).

Preservatives can desirably be incorporated into the compositions of this invention to protect against the growth of potentially harmful microorganisms. While it is in the aqueous phase that microorganisms tend to grow, microorganisms can also reside in the oil phase. As such, preservatives which have solubility in both water and oil are preferably employed in the present compositions. Suitable traditional preservatives are alkyl esters of parahydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are methyl paraben, propyl paraben, butyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are employed in amounts ranging from about 0.01% to about 2% by weight of the composition. In a preferred embodiment, preservatives (antimicrobials) will be absent from the composition with the exception of pentylene glycol which has preservative activity.

Minor adjunct ingredients may also be included such as fragrances, antifoam agents, opacifiers and colorants, each in their effective amounts to accomplish their respective functions.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated.

EXAMPLES 1–8

A series of cosmetic compositions typical of the present invention are reported in the Table below. These are gel emulsions.

TABLE I

| INGREDIENT | EXAMPLE (WEIGHT %) | | | | | | | |
|---|---|---|---|---|---|---|---|---|
| | 1 | 2 | 3 | 4 | 5 | 6 | 7 | 8 |
| PHASE A | | | | | | | | |
| Carbopol 1382 ® (2% Active in water) | 20.0 | 20.0 | 20.0 | 20.0 | 20.0 | 20.0 | 20.0 | 20.0 |
| Disodium EDTA | 0.1 | 0.1 | 0.1 | 0.1 | 0.1 | 0.1 | 0.1 | 0.1 |
| Butylene Glycol | 1.7 | 1.7 | 1.7 | 1.7 | 1.7 | 1.7 | 1.7 | 1.7 |
| Glycerin | 2.0 | 2.0 | 2.0 | 2.0 | 2.0 | 2.0 | 2.0 | 2.0 |
| Pentylene Glycol | 1.0 | 1.0 | 1.0 | 1.0 | 5.0 | 10.0 | 10.0 | 2.0 |
| Allantoin | 0.2 | 0.2 | 0.2 | 0.2 | 0.2 | 0.2 | 0.2 | 0.2 |
| Trehalose | 0.5 | 0.5 | 0.5 | 0.5 | 0.5 | 0.5 | 0.5 | 0.5 |
| Water | Bal. | Bal. | Bal. | Bal. | Bal. | Bal. | Bal. | Bal. |
| PHASE B | | | | | | | | |
| Herbal Extract | 1.0 | 1.0 | 1.0 | 1.0 | 1.0 | 1.0 | 1.0 | 1.0 |
| Borage Oil | 1.0 | 1.0 | 1.0 | 1.0 | 1.0 | 1.0 | 1.0 | 1.0 |
| Tridecyl Salicylate | 2.0 | 2.0 | 2.0 | 2.0 | 2.0 | 2.0 | 2.0 | 2.0 |
| Stearyl Alcohol | 1.3 | 1.3 | 1.3 | 1.3 | 1.3 | 1.3 | 1.3 | 1.3 |
| Steareth-2 | 1.0 | 1.0 | 1.0 | 1.0 | 1.0 | 1.0 | 1.0 | 1.0 |
| Steareth-21 | 1.0 | 1.0 | 1.0 | 1.0 | 1.0 | 1.0 | 1.0 | 1.0 |
| Amphisol A ® | 0.5 | 0.5 | 0.5 | 0.5 | 0.5 | 0.5 | 0.5 | 0.5 |
| Vitamin E Acetate | 0.5 | 0.5 | 0.5 | 0.5 | 0.5 | 0.5 | 0.5 | 0.5 |
| Phenonip ® | 0.4 | 0.4 | 0.4 | 0.4 | 0.4 | 0.4 | 0.4 | 0.4 |
| PHASE C | | | | | | | | |
| Silicone Copolyol (EM-97) | 1.0 | 1.0 | 1.0 | 1.0 | 1.0 | 1.0 | 1.0 | 1.0 |
| Cyclomethicone (DC 345 ®) | 3.0 | 3.0 | 3.0 | 3.0 | 3.0 | 3.0 | 3.0 | 3.0 |
| Silicone Elastomer Mixture (35% Elastomer Solids in Cyclomethicone) | 35.0 | 30.0 | 25.0 | 20.0 | 10.0 | 5.0 | 55.0 | 35.0 |
| Fragrance | 0.15 | 0.15 | 0.15 | 0.15 | 0.15 | 0.15 | 0.15 | 0.15 |
| PHASE D | | | | | | | | |
| Water | 2.0 | 2.0 | 2.0 | 2.0 | 2.0 | 2.0 | 2.0 | 2.0 |
| Potassium Hydroxide Solution (45% Active) | 0.7 | 0.7 | 0.7 | 0.7 | 0.7 | 0.7 | 0.7 | 0.7 |
| DL-Panthenol | 0.2 | 0.2 | 0.2 | 0.2 | 0.2 | 0.2 | 0.2 | 0.2 |
| PHASE E | | | | | | | | |
| Algae Extract | 1.0 | 1.0 | 1.0 | 1.0 | 1.0 | 1.0 | 1.0 | 1.0 |
| Phytoester | 1.0 | 1.0 | 1.0 | 1.0 | 1.0 | 1.0 | 1.0 | 1.0 |
| Water | 5.0 | 5.0 | 5.0 | 5.0 | 5.0 | 5.0 | 5.0 | 5.0 |

EXAMPLE 9

This example provides physical stability data on gel emulsions of the present invention. A base composition essentially identical to Example 1 (but without butylene glycol or glycerin) was employed as a vehicle for storage stability testing. Formulation A included 5% pentylene glycol within the base composition. Formulation B included 5% propylene glycol as a replacement for the pentylene glycol. Table II reports the viscosity change effects of freeze and thaw cycling (between 4° C. and 43° C.).

TABLE II

The Effect of Freeze and Thaw Cycle On Viscosity (cps)

| | FORMULATION | |
|---|---|---|
| CYCLE | A (Pentylene Glycol) | B (Propylene Glycol) |
| Initial | 38,000 | 41,000 |
| Cycle-1 | 48,000 | 24,000 |
| Cycle-2 | 53,000 | 8,000 |
| Cycle-3 | 50,000 | 6,000 |

Temperature cycling resulted in a slight increase in viscosity of the pentylene glycol/elastomer Formulation A. The change from 38,000 cps to 50,000 cps represents an increase of about 32%. Cycling decreased the viscosity of Formulation B from 41,000 cps to 6,000 cps. The change represented a 75% viscosity decrease. Thus, pentylene glycol had a viscosity stabilizing effect on the elastomer composition in contrast to the steep decline in viscosity utilizing propylene glycol.

EXAMPLE 9

Clinical moisturization studies were conducted to evaluate the effect of pentylene glycol in combination with polysiloxane elastomer. Formulation C was essentially identical to that of Example 1. Formulation D was equivalent to Formulation C except elastomer was absent from the former. Moisturization evaluations were performed utilizing the Skicon method. Table III reports moisturization results.

TABLE III

Moisturization Boost (1 Hour)

| FORMULATION | SKICON VALUES (Average Change From Base Line) |
|---|---|
| Untreated (Control) | 5.84 |
| C (Elastomer) | 20.13 |
| D No Elastomer | 15.40 |

Formulation C containing a combination of pentylene glycol and elastomer exhibited a large increase in moisturization over the untreated skin. Deletion of elastomer in Formulation D resulted in a decrease in moisturization relative to In Formulation C. These results indicate that moisturization benefits are achievable from a combination of pentylene glycol and polysiloxane elastomer.

The foregoing description and examples illustrate selected embodiments of the present invention. In light thereof variations and modifications will be suggested to one skilled in the art, all of which are within the spirit and purview of this invention.

What is claimed is:

1. A cosmetic composition in emulsion form for providing skin care, which comprises:

(i) from about 0.1 to about 30%, by weight, of a polysiloxane elastomer;

(ii) from about 5 to about 80%, by weight, of a volatile siloxane;

(iii) from about 10 to about 95%, by weight, of water; and (iv) from about 0.1 to about 40%, by weight, of pentylene glycol to provide a stabilized emulsion.

2. The composition according to claim 1, wherein the emulsion is selected from the group consisting of water-in-oil emulsions and oil-in-water emulsions.

3. The composition according to claim 1 wherein the elastomer is a crosslinked non-emulsifying polysiloxane.

4. The composition according to claim 1 wherein the elastomer is a Dimethicone/Vinyl Dimethicone Crosspolymer.

5. The composition according to claim 1 wherein preservatives other than pentylene glycol are absent.

6. The composition according to claim 1 further comprising a pair of nonionic surfactants and an anionic surfactant in a weight ratio total nonionic to anionic surfactant of about 20:1 to about 1:2.

7. The composition according to claim 6 wherein the anionic surfactant is a $C_8$–$C_{20}$ alkyl phosphate salt.

* * * * *